United States Patent [19]

Heron

[11] Patent Number: 5,349,849
[45] Date of Patent: Sep. 27, 1994

[54] LIQUID FLOW SYSTEM HAVING INPROVED APPARATUS FOR DETERMINING PARTICULATE CONTAMINATION LEVEL

[75] Inventor: Roger A. Heron, Stagsden, England

[73] Assignee: British Technology Group Limited, London, United Kingdom

[21] Appl. No.: 30,313

[22] PCT Filed: Sep. 24, 1991

[86] PCT No.: PCT/GB91/01640

§ 371 Date: Apr. 27, 1993

§ 102(e) Date: Apr. 27, 1993

[87] PCT Pub. No.: WO92/05424

PCT Pub. Date: Apr. 2, 1992

[30] Foreign Application Priority Data

Sep. 25, 1990 [GB] United Kingdom ............ 9020811.7

[51] Int. Cl.$^5$ ............................................. G01N 15/06
[52] U.S. Cl. ....................................... 73/61.73; 73/61.42
[58] Field of Search .................. 73/53.01, 61.42, 61.71, 73/61.73

[56] References Cited

U.S. PATENT DOCUMENTS

| | | | |
|---|---|---|---|
| 2,043,964 | 6/1936 | Piel | 73/61.73 |
| 3,050,987 | 8/1962 | Osgood | 73/61.73 |
| 3,678,881 | 7/1972 | Shinn | 73/53.01 |
| 4,468,954 | 9/1984 | Lnactot et al. | 73/61.73 |
| 4,495,799 | 1/1985 | Fisher et al. | 73/61.73 |
| 4,599,893 | 7/1986 | Fisher et al. | 73/61.73 |

FOREIGN PATENT DOCUMENTS

| | | |
|---|---|---|
| 81340 | 6/1983 | European Pat. Off. . |
| 101263 | 2/1984 | European Pat. Off. . |
| 123494 | 10/1984 | European Pat. Off. . |
| 2112530 | 7/1983 | United Kingdom . |
| 2141240 | 12/1984 | United Kingdom . |

*Primary Examiner*—Hezron E. Williams
*Assistant Examiner*—Michael Brock
*Attorney, Agent, or Firm*—Cushman, Darby & Cushman

[57] ABSTRACT

In a liquid flow system including conduit through which liquid is pumped and including an apparatus for determining the level of particulate contamination within the liquid the apparatus includes a valve in communication with the conduit having a valve member moveable relative to a valve housing in which the valve member can be set relative to the housing to define a narrow clearance through which flow takes place. A mechanism is provided for interrupting the normal pumped flow of liquid through the system and, when it is so interrupted, for causing liquid to flow through the valve clearance instead. A monitor is provided for monitoring the volume of liquid so passed, and for deriving a measure of the degree of contamination of the liquid in the system. The flow through the narrow clearance is in direction substantially at right angles to that of the relative movement of the valve member and valve housing.

13 Claims, 5 Drawing Sheets

LIQUID FLOW SYSTEM HAVING INPROVED APPARATUS FOR DETERMINING PARTICULATE CONTAMINATION LEVEL

This Invention relates to hydraulic and other liquid flow systems, and tn particular to a mechanism by which the degree of contamination of the fluid tn such a system can periodically be measured. Examples of such mechanisms, which have already been put into use, are described in Patent Specifications GB-B-2112530 and GB-B-2141240. Each of those two specifications describes a mechanism which periodically tests the contamination of the system fluid by isolating a sample volume of that fluid, using a dedicated power source to pass that isolated volume through a small orifice of a particular kind, measuring the degree of contamination by reference to how quickly the orifice becomes blocked, and then re-setting the mechanism In readiness for the next test. The mechanisms described In both specifications are aimed primarily at testing for the presence of particles of metal and other very hard materials that are the typical contaminants of many hydraulic fluid power systems. Consequently both specifications state that the orifices should be of the kind. sometimes referred to as viscous-loss, tn which the accumulation of small particles of metal or other such materials tends to vary predictably with the volume of hydraulic fluid that has passed through the orifice, assuming a constant degree of contamination of that fluid. The typical viscous-loss orifices described with reference to the drawings of those specifications are all defined between spool-like members and the cylindrical housings in which they move, and are tn the form of small annular clearances between spool and housing and coaxial with both of them.

Such clearances, whilst suitable for hydraulic fluids contaminated by metal or like hard particles with a typical maximum dimension of the order of say 1½–5 microns, are much less so for fine particulate slurries of the kind commonly processed in the china clay industry for example, in which the typical contaminant particles are softer, plate-like in shape, and with a much greater maximum dimension of the order say of 35–50 microns. Such particles tend not to accumulate at the mouth of an annular, viscous-loss orifice as just described, but to intrude into the orifice and jam it. This not only affects the result of the test by restricting the orifice much more quickly than would be the case if the particles came to rest at the orifice mouth, but also tends to interfere with the subsequent axial movement of the spool, at the end of the test, to clear the orifice and re-set it for the next test.

One aim of the present invention is to provide an alternative mechanism more suitable to measure the contamination of fluids by such larger and softer particles. The invention also facilitates using the main pumping source of the system, rather than dedicated sources as described in the two quoted prior specifIcations, as the power source for conducting the tests also.

The invention is described by the claims, the contents of which are to be read as included within the disclosure of this specification, and the invention includes liquid flow systems as described by way of example with reference to the accompanying drawings in which:

Figure 1:
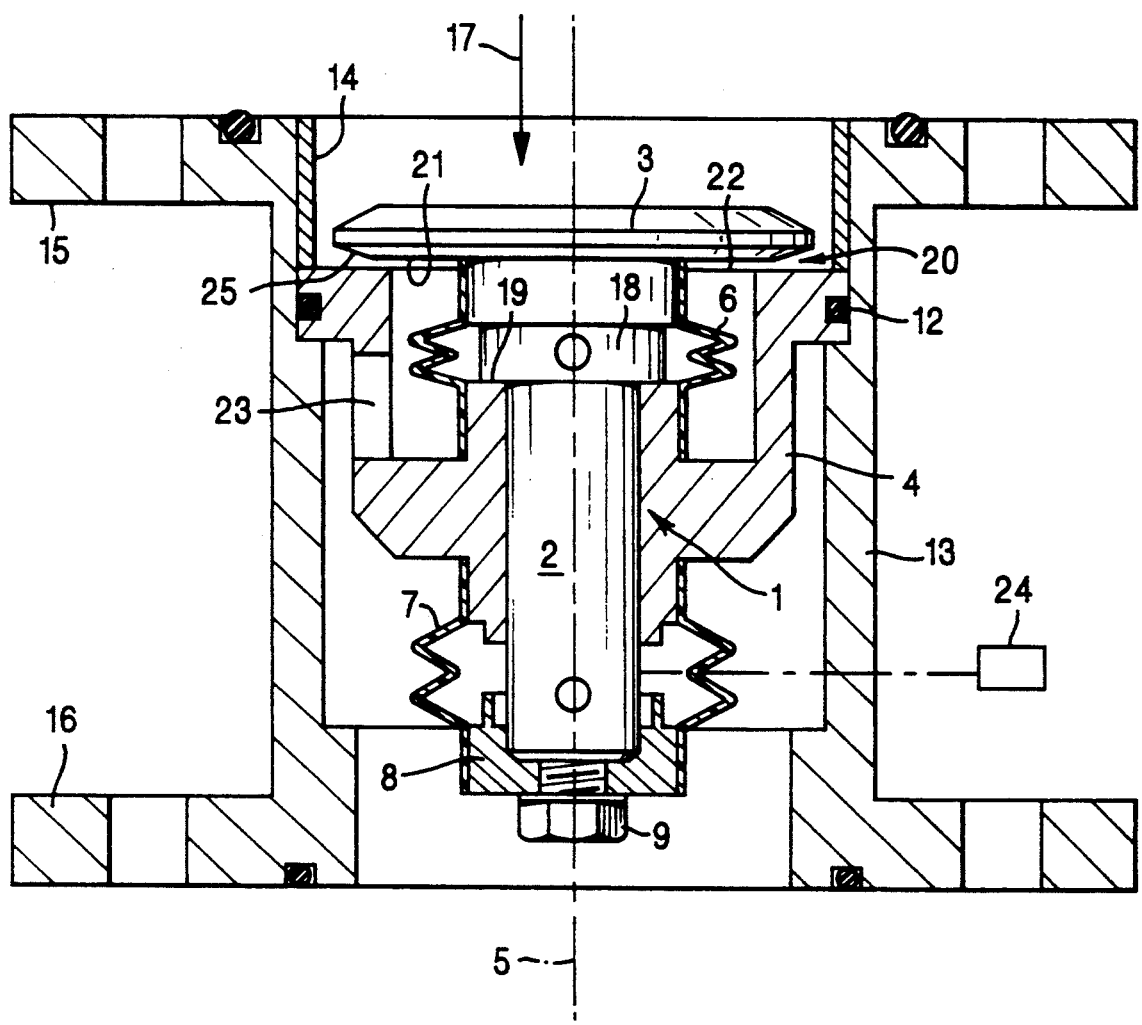
FIG. 1 is a cross section through a valve.

In FIG. 1 a valve member 1, comprising a stem 2 and a head 3, can slide within a housing 4 in the direction of their common axis 5. Bellows 6 and 7 prevent access of contaminants to the surfaces of member 1 and housing 4 that are in sliding contact with each other. At the end remote from head 3, a flange 8 is fixed to stem 2 by a screw 9. A ring seal 12 makes fluid-tight contact between housing 4 and a pipe section 13, within which the housing is held in place by a securing collar 14. End flanges 15, 16 are provided for bolting section 13 to adjacent lengths of piping (not shown). When a test for contaminants is in progress, flow of fluid through pipe section 13 is in the direction of arrow 17, which moves valve member 1 in that direction until a flange 18 on stem 2 abuts a shoulder 19 on housing 4, and so sets a narrow disc-shaped clearance 20 between the underside 21 of head 3 and the end face 22 of housing 4. At the end of such a test, or in normal flow If pipe section 13 is located in-line within the normal flow line of the system, fluid flow in the reverse direction to 17 will pass through a substantial aperture 23 in housing 4, lift head 3 off face 22 to the extent allowed by the elongation of bellows 6 and 7, and allow substantially unimpeded flow. Alternatively or In addition—in the latter case for Instance for use in emergency—valve member 1 could be moveable by remotely-controlled operating equipment indicated in outline only at 24. It would also of course be possible, if suitable access to the Interior of pipe section 13 were provided, to move valve member back and forth manually within housing 4 and so, for instance to clean the two parts and re-set them between tests.

The disc-like shape of clearance 20, with its tapering entry provided by the chamfered face 25 on head 3, makes it well-suited to receiving and in due course becoming blocked by the soft, plate-shaped impurities that have already been described. Also, the fact that at the end of a test the valve member 1 and housing 4 are moved apart under substantial force, and in a direction at right angles to the radial plane of the clearance 20, helps to minimise the chance that the sticky contaminant particles jam in the clearance and prevent the valve from opening again, as would be likely if the valve were of the spool-type described in specifications GB-B-2112530 and GB-B-2141240 for instance.

Figure 2:
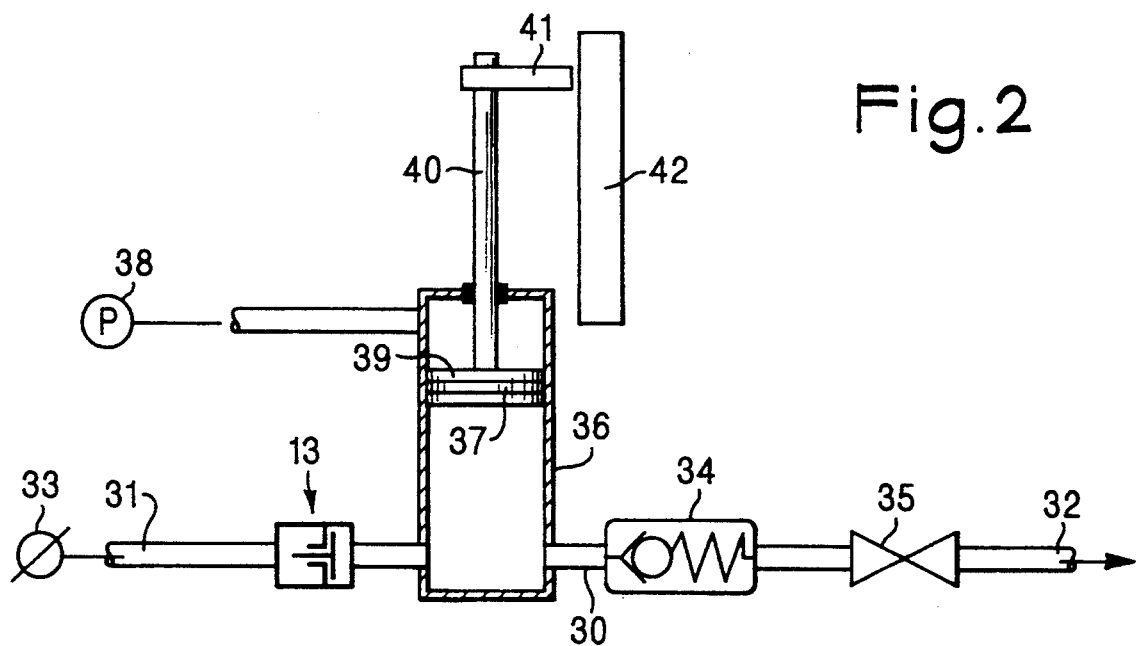
FIGS. 2 and 3 are schematic circuit diagrams showing alternative arrangements of such a valve within a hydraulic flow system.
Figure 3:
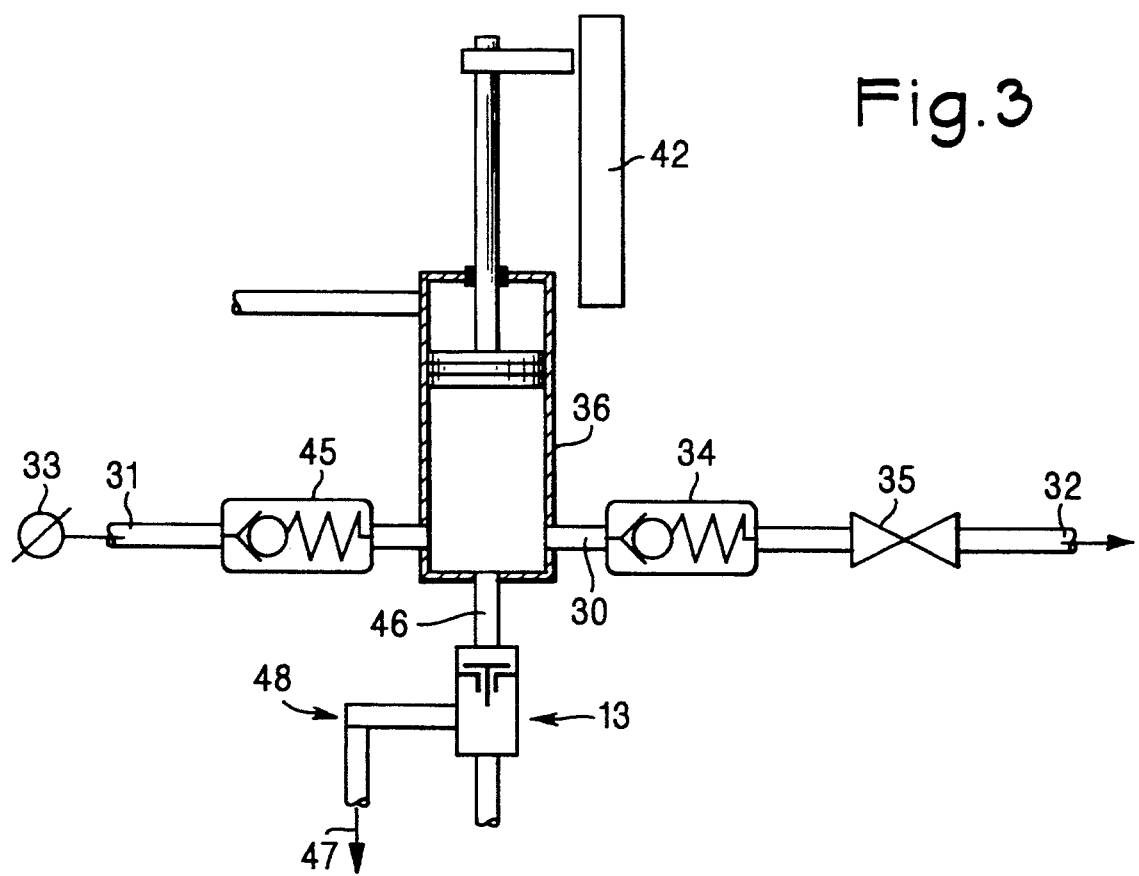

In FIGS. 2 and 3 the main flow line 30 of a hydraulic flow system carries fluid from an inlet 31 to an outlet 32, between which the flow is driven in normal use by a pump indicated at 33. At all times a non-return valve 34 prevents back flow, and during normal use a shut-off valve 35 is open. In both of these Figures a sampling cylinder 36 is located in series with line 30, and a plunger 37 is moveable within that cylinder by a fluid power source 38 in communication with the reverse face 39 of the plunger. A rod 40, carried by the plunger, co-operates by way of a link 41 with displacementmeasuring means 42 by which the location of plunger 37 within cylinder 36 is monitored. Using the apparatus of FIG. 2, when it is desired to test the contamination of the fluid flowing within line 30, power source 38 is operated to withdraw plunger 37 to the top of cylinder 36, so filling the cylinder with fluid. Pump 33 is now stopped and valve 35 shut. Source 38 then drives plunger 37 downwards, expelling fluid from the cylinder in the reverse direction up line 30, through pipe section 13 which is located in-line within 30, in the direction indicated by arrow 17 in FIG. 1, moving the valve member 1 so that flange 18 meets shoulder 19 and clearance 20 is established. The degree of contamination of the fluid is indicated by how far plunger 37 descends before clearance 20 becomes blocked and prevents further descent: for instance full descent of the piston without obstruction indicates little contamination, and only a short descent heavy contamination, the length of the descent being indicated by monitor 42 and representing the volume of fluid that has been passed out of cylinder 36 and through clearance 20. After the test, valve 35 is re-opened and pump 33 restarted, and the natural effect of the resumed normal flow within line 30, perhaps assisted by automatic (24) or manual means, as already described, is to move valve member 1 by extending bellows 6, 7, and so to open clearance 20 again. In the alternative apparatus of FIG. 3, an extra non-return valve 45 is provided within line 30 and pipe section 13 is located within a branch line 46 connecting cylinder 36 to exhaust 47, instead of within line 30 itself. When a contaminant test is conducted now, valve 35 and pump 33 are again shut off, and the contents of cylinder 36 are again discharged through clearance 20. The volume of fluid passed through the clearance during the test could now be measured at 48, between the valve and exhaust 47, instead of by monitor 42, and valve 45 prevents the contents of cylinder 36 from escaping backwards up line 30. After the test, because the valve is no longer in line with the main flow, positive clearance by manual and/or automatic means will be necessary.

Figure 4:
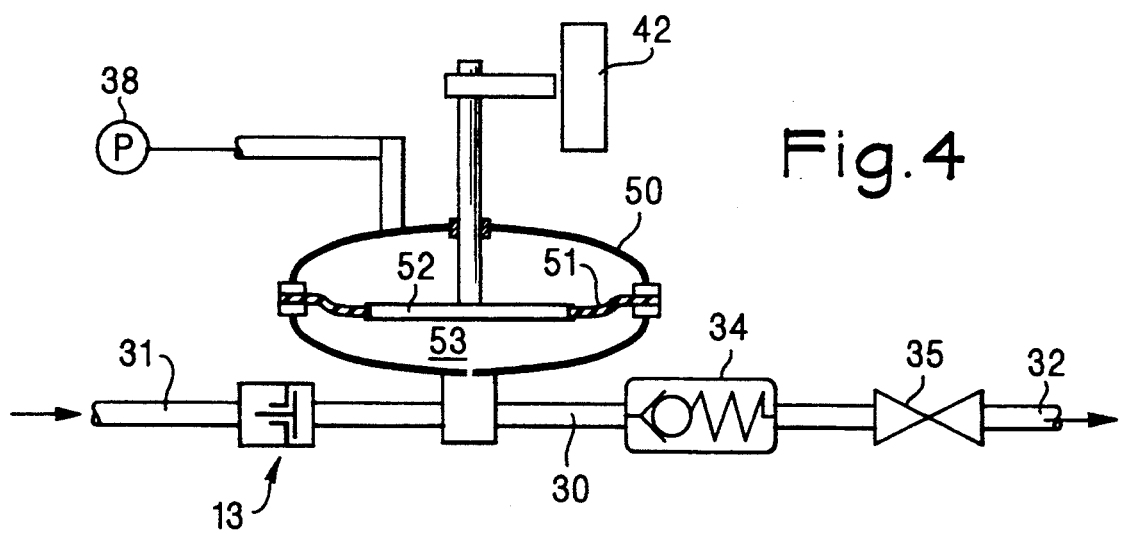
FIGS. 4 and 5 are similar to FIGS. 2 and 3, but show alternative arrangements of power source for both the system and a mechanism for determining contamination.
Figure 5:
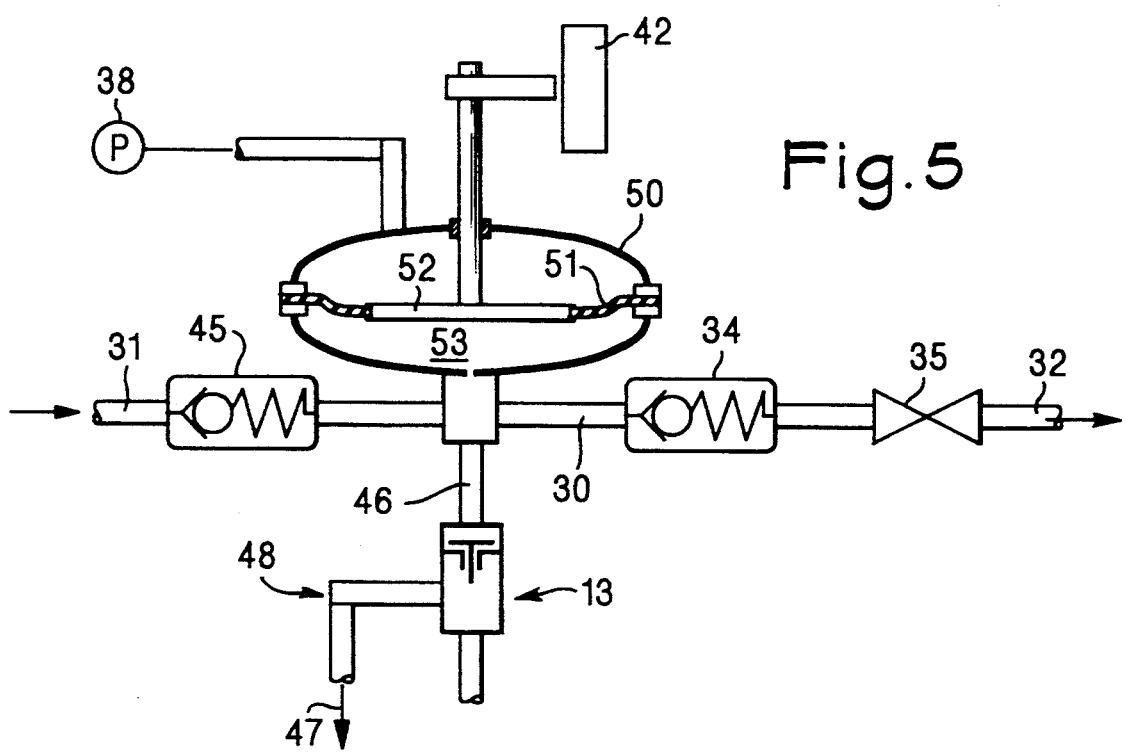

The systems of FIGS. 4 and 5 are similar to those of FIGS. 2 and 3 respectrrrely, except that main pump 33 and the cylinder/plunger unit 36, 37 are omitted and a diaphragm pump 50, driven by power source 38, which may tn practice be a pneumatic source, is substituted. In normal use, an upward stroke of diaphragm 51 and piston 52 draws fluid from inlet 31 in both of these embodiments, and a downwards stroke expels that volume through non-return valve 34 and open valve 35 towards outlet 32. When a contaminant test is to be conducted, an upward stroke of 51/52 fills the lower chamber 53 of pump 50 with a test sample, after which valve 35 is closed and the sample is discharged through the valve in pipe section 13 Just as already described with reference to FIGS. 2 and 3.

Figure 6:
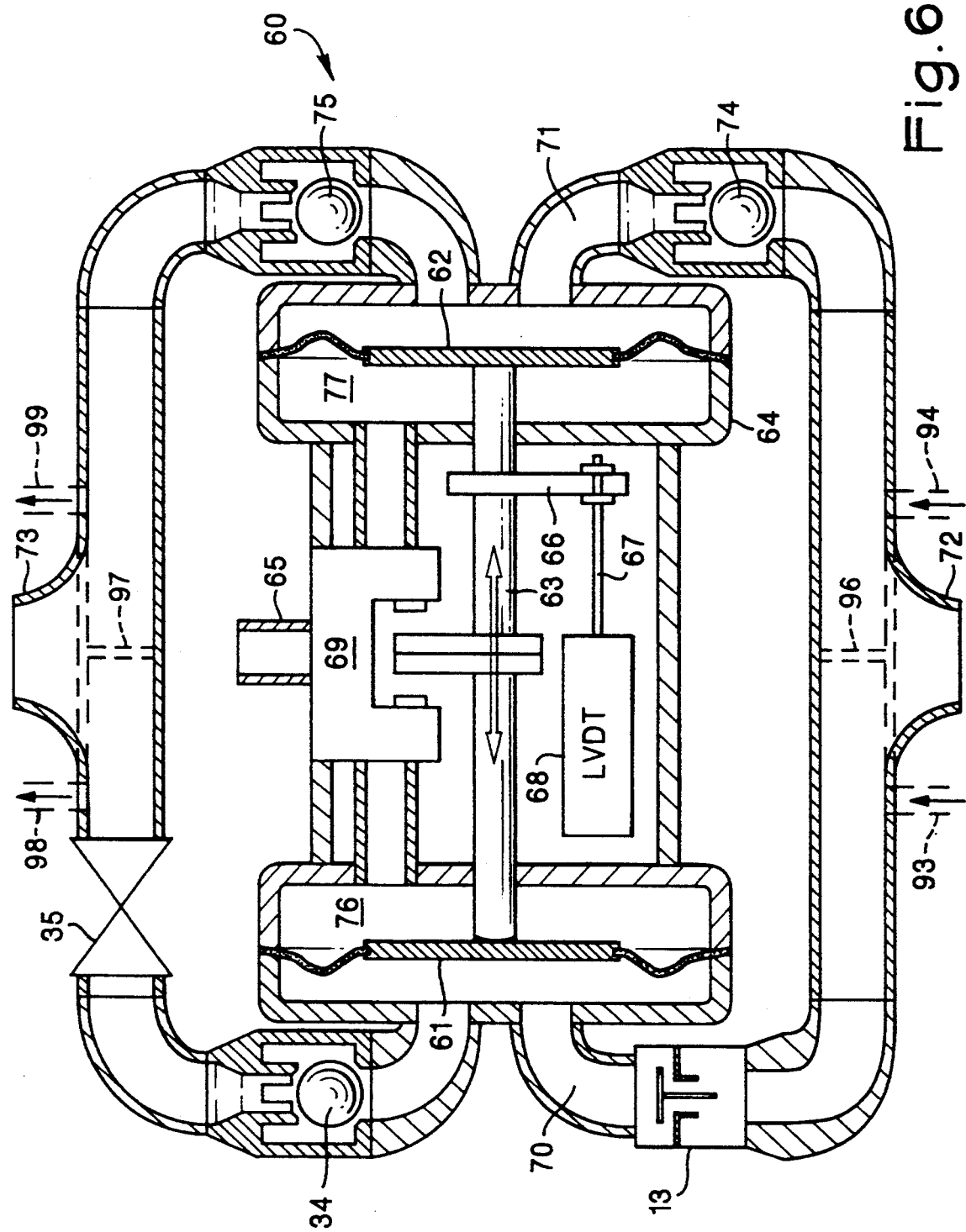
FIG. 6 is a cross section through an alternative power source for such a system and mechanism.

In FIG. 6 the single-acting diaphragm pump of FIGS. 4 and 5 is replaced by a double-acting diaphragm pump 60 comprising opposed piston/diaphragm units 61, 62 mounted on a common shaft 63 and within a housing 64. The pump is pneumatically-driven by air delivered by an air pump (not shown in FIG. 6) and entering the housing by way of inlet 65. The inlet is connected to an air valve 69, which controls the flow of air to the separated volumes 76, 77 of the interior of housing 64, whereby to drive the two units 61, 62. Shaft 63 is also connected by a link 66 to the plunger 67 of a linear voltage differential transformer (LVDT) 68, which serves a comparable function to the monitor 42 shown in FIGS. 2 to 5. As shown in full lines tn FIG. 6, the two ends of pump 60 exert a pumping action in separate parallel conduits 70 and 71, which are connected by a common inlet 72 to the upstream part of line 30 and by a common outlet 73 to the downstream part. Conduit 71 contains only two simple non-return valves 74 and 75, and therefore exerts a continuous pumping action between Inlet 31 and outlet 32 of line 30 whenever pump 60 is acting. Conduit 70, however, contains pipe section 13, non-return valve 34 and shut of valve 35 exactly as shown in FIGS. 2 and 4, which are operated exactly as already described when a contaminant test is performed, without interfering with the continuing forward flow of fluid through conduit 71.

Figure 7:
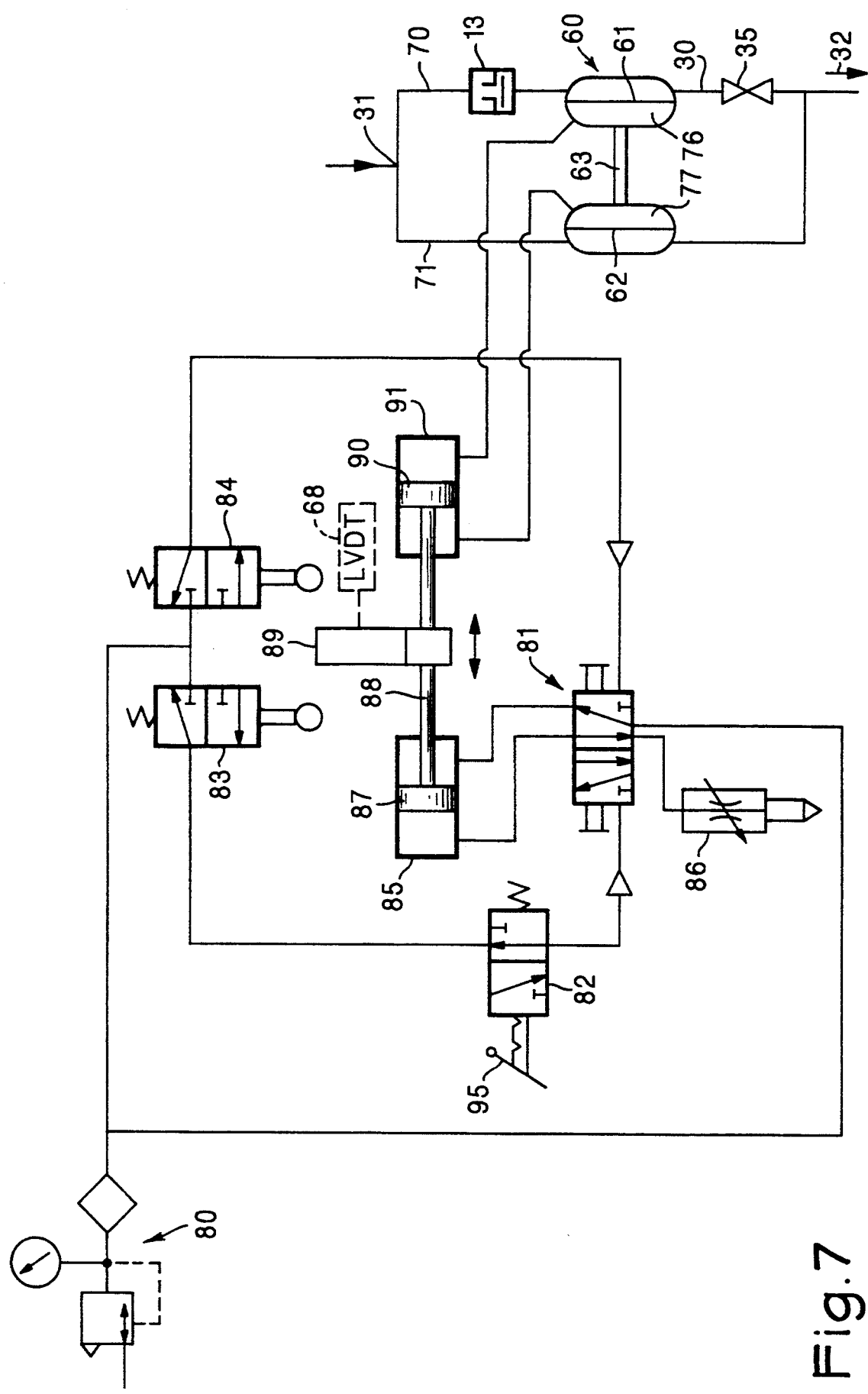
FIG. 7 is a schematic layout showing the controls and auxiliary power sources for a system including the pump of FIG. 6.

FIG. 7 shows the rudiments of one control system by which a pump, hydraulically-driven but otherwise similar to item 60 of FIG. 6, might be operated. A supply 80 delivers compressed air, at say 7 Bar maximum pressure, to a pneumatic control valve 81 which is connected to a further control unit 82, to two limit switches 83 and 84, to the opposite ends of a pneumatic cylinder 85, and to a conventional vent/control 86. A piston 87, mounted within 85, is carried on one end of a rod 88 which also carries a trip member 89 and a piston 90 which moves within a hydraulic cylinder 91, the two ends of which are connected to the two internal volumes 76 and 77 of pump 60. Shut-off valve 35 fulfills the same function as in FIGS. 2 to 6. In normal operation of the system, during which liquid is pumped continually from inlet 31 to outlet 32 down both of conduits 70 and 71, control valve 81 operates to drive piston 87 pneumatically to the right until trip 89 contacts the sensor of switch 84, when the supply of air to cylinder 85 is reversed and piston 87 travels leftwards until the sensor of valve 83 is tripped and the pneumatic supply reverses once again. The pneumatically-driven motion of piston 87 within cylinder 85 is translated by piston 90 into a hydraulic pumping action within cylinder 91, and so into an alternating hydraulic driving action upon diaphragm/pistons 61 and 62 of pump 60. When a contaminant test is required, valve 82 is actuated (as shown, by operation of control member 95) so that as pistons 87 and 90 begin their next rightwards stroke valve 35 shuts and diaphragm/piston 61 discharges a test sample through the valve 1, 4 in pipe section 13. The same operation of valve 82 also operates, if necessary, to disable valve 84 to ensure that piston 90 is capable of driving piston/diaphragm 61 through the maximum stroke that the test might require. As indicated in outline, the LVDT 68 of FIG. 6 could now if desired be attached to the trip 89, rather than to the common rod 63 of diaphragm/pistons 61 and 62, the movements of pistons 90 and 61, 62 being proportional because the pistons are in contact with same mass of incompressible liquid.

In an alternative embodiment of the invention to that shown in full lines in FIG. 6, the chamber of pump 60 could be divided in two by a wall shown in broken lines at 96, 97 and each of conduits 70 and 71 could have separate inlets (93, 94) and outlets (98, 99) to upstream and downstream parts of the entire flow system, so that conduits 70, 71 become parts of two separate flow lines, instead of short parallel branches within a single line. In this case, if it is wished at any time to test the contamination of the fluid within conduit 71, that conduit would need to be provided with its own shut-off valve (35) and test valve unit (13), just like conduit 70.

I claim:

1. A liquid flow system having conduit means through which liquid is pumped in normal use, and including means for determining the level of particulate contamination within that liquid, the determining means comprising:

a valve in communication with the conduit means and comprising a valve housing and a valve member moveable relatively to said valve housing in which the valve member can be set relative to the valve housing to define a predetermined clearance through which flow takes place;

means for interrupting the normal pumped flow of liquid to flow instead through the said predetermined clearance, and means for monitoring the volume of liquid passed and for deriving a measure of the degree of contamination of the liquid in the system, said predetermined clearance being oriented for causing the flow through said predetermined clearance to be in a direction substantially at right angles to that of the relative movement of said valve member and valve housing.

2. A flow system according to claim 1 wherein the valve member comprises a stem surmounted by a head, and said predetermined clearance is defined between an underside of the head and a confronting surface of the valve housing.

3. A flow system according to claim 1 wherein the valve is situated in a branch to the main flow conduit.

4. A flow system according to claim 3, further comprising remotely-controlled means for clearing and resetting the valve after each contaminant determination.

5. A flow system according to claim 1 wherein the valve is located within the main liquid flow conduit.

6. A flow system according to claim 5 wherein the valve housing and member take up one of two relative positions automatically in response to the direction of the liquid flow through the valve, in which during normal flow they take up a first position offering minimum resistance to that flow, and in which while contamination is being determined the flow through the valve is reversed and they take up a second position in which said predetermined clearance is defined between them.

7. A flow system according to claim 1 wherein the flow of liquid through the valve during a contaminant determination is driven by means other than the pump that drives the normal liquid flow through the system.

8. A fluid flow system according to claim 1 wherein the flow of liquid through the valve during a contaminant determination is driven by the same pump that drives the normal liquid flow through the system.

9. A flow system according to claim 8 wherein the pump is of diaphragm type.

10. A flow system according to claim 9 wherein a double-ended, double-acting diaphragm pump is used, and in which both ends of the pump exert a pumping action during normal flow through the system.

11. A flow system according to claim 10 wherein the two ends of the diaphragm pump are connected in parallel to the same inlet within the system, and deliver in parallel to the same outlet.

12. A flow system according to claim 10 wherein the two ends of the hydraulic pump drive the flow in separate flow lines within the system.

13. A flow system according to claim 1 wherein the pump is air-driven.

* * * * *